(12) United States Patent
Sharma et al.

(10) Patent No.: US 9,863,893 B2
(45) Date of Patent: Jan. 9, 2018

(54) SENSOR APPARATUS FOR MEASUREMENT OF MATERIAL PROPERTIES

(71) Applicant: General Electric Company, New York, NY (US)

(72) Inventors: Praful Sharma, Bangalore (IN); Manoj Kumar Koyithitta Meethal, Bangalore (IN); Aparna Chakrapani Sheila-Vadde, Bangalore (IN); Suma Memana Narayana Bhat, Bangalore (IN); Vipin Velayudhan, Kerala (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 221 days.

(21) Appl. No.: 14/396,580

(22) PCT Filed: May 29, 2013

(86) PCT No.: PCT/US2013/042955
§ 371 (c)(1),
(2) Date: Oct. 23, 2014

(87) PCT Pub. No.: WO2013/181173
PCT Pub. Date: Dec. 5, 2013

(65) Prior Publication Data
US 2015/0097579 A1    Apr. 9, 2015

(30) Foreign Application Priority Data
May 30, 2012  (IN) .......................... 2174/CHE/2012

(51) Int. Cl.
*G01N 22/00*    (2006.01)
*G01R 27/06*    (2006.01)
(Continued)

(52) U.S. Cl.
CPC .............. *G01N 22/00* (2013.01); *G01R 27/06* (2013.01); *G01R 27/02* (2013.01); *G01R 27/04* (2013.01)

(58) Field of Classification Search
CPC ........ G01N 22/00; G01R 27/06; G01R 27/00; G01R 27/02; G01R 27/04
(Continued)

(56) References Cited

U.S. PATENT DOCUMENTS

| | | | |
|---|---|---|---|
| 4,062,010 A | 12/1977 | Young et al. | |
| 4,902,961 A | 2/1990 | De et al. | |

(Continued)

FOREIGN PATENT DOCUMENTS

| | | |
|---|---|---|
| CN | 101103256 A | 1/2008 |
| CN | 101919114 A | 12/2010 |

(Continued)

OTHER PUBLICATIONS

Rajab et al., "Size reduction of micro strip antennas using metamaterials", vol. No. 2B, pp. 296-299, Jul. 2005.
(Continued)

*Primary Examiner* — Hoai-An D Nguyen
(74) *Attorney, Agent, or Firm* — GE Global Patent Operation; Laura L. Pollander

(57) ABSTRACT

A material constituent sensor includes one or more metamaterial assisted antennas located to probe a material that is a multiphase composition. A signal source excites at least one metamaterial assisted antenna in a desired range of radio frequency (RF) signals, a desired range of microwave signals, or a combination RF signals and microwave signals. A data processing device is programmed to estimate material constituent fractions associated with the probed material based on amplitude data, phase data, frequency shift data, or a combination of amplitude data, phase data and frequency (Continued)

shift data in response to transmitted energy from at least one excited metamaterial assisted antenna, reflected energy received by at least one metamaterial assisted antenna, frequency shift data, or a combination of the transmitted energy, the reflected energy and the frequency shift.

20 Claims, 5 Drawing Sheets

(51) Int. Cl.
  *G01R 27/04* (2006.01)
  *G01R 27/02* (2006.01)
(58) Field of Classification Search
  USPC .......................................... 324/600, 629, 637
  See application file for complete search history.

(56) References Cited

U.S. PATENT DOCUMENTS

| | | | |
|---|---|---|---|
| 4,924,695 A | 5/1990 | Kolpak | |
| 5,005,015 A | 4/1991 | Dehn et al. | |
| 5,025,222 A | 6/1991 | Scott et al. | |
| 5,101,163 A | 3/1992 | Agar | |
| 5,103,181 A | 4/1992 | Gaisford et al. | |
| 5,485,743 A | 1/1996 | Taherian et al. | |
| 5,550,537 A * | 8/1996 | Perdue ................... | G01F 1/66 177/16 |
| 5,675,259 A | 10/1997 | Arndt et al. | |
| 5,741,979 A | 4/1998 | Arndt et al. | |
| 7,135,872 B2 | 11/2006 | Bentolila et al. | |
| 7,293,471 B2 | 11/2007 | Lund Bo et al. | |
| 7,456,744 B2 | 11/2008 | Kuhns et al. | |
| 7,469,188 B2 | 12/2008 | Wee | |
| 7,474,971 B2 | 1/2009 | Hu et al. | |
| 7,535,364 B2 | 5/2009 | Sakama et al. | |
| 7,775,083 B2 | 8/2010 | Potyrailo et al. | |
| 7,791,355 B1 * | 9/2010 | Esher ..................... | G01N 22/00 324/637 |
| 7,889,127 B2 | 2/2011 | Sajuyigbe et al. | |
| 7,969,312 B2 * | 6/2011 | Abrunhosa ............. | G01V 3/38 340/551 |
| 8,644,197 B2 | 2/2014 | Lee et al. | |
| 8,698,700 B2 | 4/2014 | Pathak et al. | |
| 8,742,768 B1 * | 6/2014 | Pelletier ................ | G01N 22/04 324/617 |
| 8,921,789 B2 * | 12/2014 | Pryce .................. | G01N 21/3581 250/338.1 |
| 2002/0050828 A1 | 5/2002 | Seward, IV et al. | |
| 2002/0180460 A1 * | 12/2002 | Geisel ................... | G01R 15/06 324/628 |
| 2003/0036674 A1 * | 2/2003 | Bouton .................. | A61B 5/05 600/12 |
| 2004/0233458 A1 | 11/2004 | Frick | |
| 2005/0264302 A1 | 12/2005 | Mohajer et al. | |
| 2006/0152227 A1 | 7/2006 | Hammer | |
| 2008/0087099 A1 | 4/2008 | Allenberg et al. | |
| 2008/0192827 A1 | 8/2008 | Beric et al. | |
| 2008/0266028 A1 * | 10/2008 | Wyland ................... | H01L 23/64 333/204 |
| 2008/0319685 A1 | 12/2008 | Xie et al. | |
| 2009/0126502 A1 | 5/2009 | Wee et al. | |
| 2009/0140946 A1 | 6/2009 | Ziolkowski et al. | |
| 2010/0060544 A1 | 3/2010 | Penev et al. | |
| 2010/0141358 A1 * | 6/2010 | Akyurtlu ................. | H01P 1/20 333/219.1 |
| 2010/0148804 A1 | 6/2010 | Jakoby et al. | |
| 2011/0026624 A1 | 2/2011 | Gummalla et al. | |
| 2011/0175789 A1 * | 7/2011 | Lee ........................ | H01Q 1/243 343/853 |
| 2011/0199273 A1 | 8/2011 | Kim et al. | |
| 2011/0199281 A1 * | 8/2011 | Morton ................... | H01Q 1/42 343/872 |
| 2011/0204891 A1 | 8/2011 | Drake et al. | |
| 2011/0290035 A1 | 12/2011 | Wee et al. | |
| 2011/0301877 A1 | 12/2011 | Wee et al. | |
| 2012/0228563 A1 * | 9/2012 | Fuller ................ | F41H 13/0043 252/582 |
| 2013/0101815 A1 * | 4/2013 | Takeguchi .............. | B29C 33/56 428/209 |
| 2016/0290935 A1 * | 10/2016 | Salvador ................ | G01N 22/04 |

FOREIGN PATENT DOCUMENTS

| | | |
|---|---|---|
| CN | 102044738 A | 5/2011 |
| CN | 102439789 A | 5/2012 |
| CN | 202217775 U | 5/2012 |
| EP | 2269266 A1 | 1/2011 |
| EP | 2297818 A1 | 3/2011 |
| EP | 2359436 A2 | 8/2011 |
| EP | 2366980 A2 | 9/2011 |
| GB | 1570039 A | 6/1980 |
| JP | 6128095 B2 | 6/1986 |
| JP | 3118297 A | 5/1991 |
| JP | 4500857 A | 2/1992 |
| JP | 56362 U | 1/1993 |
| JP | 5502939 A | 5/1993 |
| JP | 1183758 A | 3/1999 |
| JP | 2000249673 A | 9/2000 |
| JP | 2001183312 A | 7/2001 |
| JP | 2002214183 A | 7/2002 |
| JP | 2006518838 A | 8/2006 |
| JP | 2007060386 A | 3/2007 |
| JP | 2009058379 A | 3/2009 |
| JP | 2009065253 A | 3/2009 |
| JP | 2009538433 A | 11/2009 |
| WO | 915243 A1 | 4/1991 |
| WO | 0077501 A1 | 12/2000 |
| WO | 2008069670 A1 | 6/2008 |
| WO | 2008127429 A2 | 10/2008 |
| WO | 2010105230 A3 | 1/2011 |
| WO | 2012007613 A1 | 1/2012 |

OTHER PUBLICATIONS

Hsu et al., "Design of MIMO antennas with strong isolation for portable applications", pp. 1-4, Jun. 2009.
Penirschke et al., "Moisture insensitive microwave mass flow detector for particulate solids", Instrumentation and Measurement Technology Conference (I2MTC), IEEE, Piscataway, NJ, USA, pp. 1309-1313, May 3, 2010.
Ouedraogo et al., "Metamaterial inspired patch antenna miniaturization technique", Antennas and Propagation Society International Symposium (APSURSI), 2010 IEEE, pp. 1-4, Jul. 17, 2010.
Puentes et al., "Metamaterials in microwave sensing applications", IEEE Sensors Conference, Piscataway, NJ, USA, pp. 2166-2171, Nov. 4, 2010.
Ziolkowski et al., "Metamaterial-Inspired Engineering of Antennas", Proceedings of the IEEE, vol. No. 99, Issue No. 10, pp. 1720-1731, Oct. 2011.
International Search Report and Written Opinion issued in connection with corresponding PCT Application No. PCT/US2013/042955 dated Aug. 22, 2013.
Chen et al., "Transmission/Reflection methods", In: "Microwave Electronics—Measurement and Materials Characterisation", pp. 175-207, Jan. 1, 2004.
Wylie et al., "RF sensor for multiphase flow measurement through an oil pipeline", Institute of Physics Publishing, Measurement Science and Technology, vol. No. 17, pp. 2141-2149, 2006.
Non-Final Rejection towards related U.S. Appl. No. 12/916,149 dated May 8, 2013.
Non-Final Rejection towards related U.S. Appl. No. 12/916,149 dated Oct. 28, 2013.
Office Action issued in connection with related CN Application No. 201110078762.X dated Jan. 22, 2014.
Notice of Allowance issued in connection with related U.S. Appl. No. 12/916,149 dated Feb. 19, 2014.

(56) References Cited

OTHER PUBLICATIONS

Japanese Search Report issued in connection with related JP Application No. 2011-020275 dated Sep. 18, 2014.
Office Action issued in connection with related JP Application No. 2011-020275 dated Oct. 21, 2014.
Office Action issued in connection with related JP Application No. 2011-020275 dated Mar. 17, 2015.
International Search Report and Written Opinion issued in connection with related PCT Application No. PCT/US2015/030346 dated Aug. 17, 2015.
Notice of Allowance issued in connection with related JP Application No. 2011-020275 dated Aug. 25, 2015.
Office Action issued in connection with corresponding CN Application No. 201380028557.X dated Jan. 28, 2016.
European Search Report and Written Opinion issued in connection with related EP Application No. 11153061.4-1554 dated Nov. 8, 2016.
Non-Final Rejection towards related U.S. Appl. No. 14/294,215 dated May 18, 2017.

* cited by examiner

SENSOR APPARATUS FOR MEASUREMENT OF MATERIAL PROPERTIES

BACKGROUND

The subject matter of this disclosure relates generally to material property sensors, and more specifically, to a material property sensor operating in the RF/microwave region of the electromagnetic (EM) spectrum and applied to flowing and/or non-flowing material constituent fraction measurement.

Microwave sensors are often employed for multiphase flow measurement applications such as measurement of water in liquid rate (WLR) and gas fraction. Many challenges of microwave sensors are associated with the size of the antenna for lower frequencies, as the size of the antenna is related to frequency, since the lower the frequency, the larger is the antenna size. This characteristic leads to size constraints in sensor spools and also adversely affects pressure handling capability. A small size antenna allows larger pressure handling capability of the spool.

In view of the foregoing, it would be advantageous to provide an EM sensor particularly a RF/microwave sensor for multiphase flow measurement applications that allows further miniaturization of the sensor antenna, lowering of operating frequencies, enhanced evanescent wave coupling, a wider frequency band, and a higher pressure capability of spool structure.

BRIEF DESCRIPTION

Briefly, in accordance with one embodiment, a method of measuring material properties comprises placing a metamaterial assisted sensor to probe a material that may comprise a multiphase composition. An RF signal, microwave signal or both an RF signal and a microwave signal is/are generated via a signal source over a desired range of frequencies and applied to the metamaterial sensor to generate an electromagnetic (EM) field. The metamaterial assisted sensor may sense changes in the EM field when the material is fixed or when it is flowing through a conduit/pipe. Changes in EM field response are based on transmitted EM energy characteristics, reflected EM energy characteristics, frequency shift characteristics, or combinations thereof. The sensed data is transmitted to a computer or data processing device(s) programmed with transfer functions. The computer/data processing device(s) applies the transfer functions in response to the sensed data to estimate material properties or constituent fractions of the material. The estimated material properties and/or constituent fractions are transmitted to a display apparatus or data storage apparatus.

According to another embodiment, a material property sensor comprises one or more metamaterial assisted antennas placed to probe a material that may be a multiphase composition. A signal source is configured to excite at least one metamaterial assisted antenna in a desired range of radio frequency signals, a desired range of microwave signals, or a combination thereof. A computer or data processor is programmed to estimate material properties and/or constituent fractions of the probed material. The material properties and/or constituent fractions associated with the material are based on amplitude data, phase data, frequency data, or a combination thereof in response to transmitted electromagnetic (EM) energy from at least one excited metamaterial assisted antenna, reflected EM energy received by at least one metamaterial assisted antenna, or a combination thereof.

According to yet another embodiment, a material property sensor comprises one or more metamaterial assisted sensors placed to probe a material. Each metamaterial assisted sensor comprises at least one antenna configured as a transmitter of electromagnetic (EM) energy, a receiver of EM energy, or a combination thereof.

DRAWINGS

These and other features, aspects, and advantages of the present invention will become better understood when the following detailed description is read with reference to the accompanying drawings in which like characters represent like parts throughout the drawings, wherein.

While the above-identified drawing figures set forth alternative embodiments, other embodiments of the present invention are also contemplated, as noted in the discussion. In all cases, this disclosure presents illustrated embodiments of the present invention by way of representation and not limitation. Numerous other modifications and embodiments can be devised by those skilled in the art which fall within the scope and spirit of the principles of this invention.

DETAILED DESCRIPTION

Figure 1:
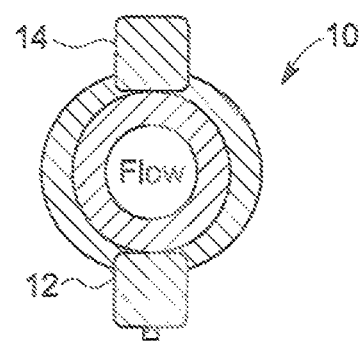
FIG. 1 is a simplified system diagram illustrating a spool cross sectional view depicting placement of metamaterial assisted antennas to form a material constituent sensor according to one embodiment.

FIG. 1 is a simplified system diagram illustrating a sensor spool cross sectional view depicting placement of two metamaterial assisted antennas 12, 14 to form a material property sensor 10 according to one embodiment. More specifically, metamaterial assisted antennas 12, 14 preferably operate in the RF/microwave region of the electromagnetic spectrum to provide a material property sensor.

The use of negative refractive index material (NRM), also known as metamaterials is employed in the sensor construction. Metamaterial is an artificial material that may exhibit EM response not readily found in nature. Negative refractive index material exhibits simultaneous negative permittivity and negative permeability. These metamaterial structures can be used for reducing the size of the EM sensor and obtain a compact sub wavelength and high performance EM sensor. According to one embodiment, each metamaterial assisted antenna 12, 14 may comprise an Rf/microwave antenna, and at least one of a feed structure, superstrate, antenna protection, such as also described in further detail herein.

The material property sensor 10 is particularly useful in measurement of constituents of a multiphase mixture/composition that could be flowing in a conduit such as a pipeline. Measurement methods for measuring multiphase compositions such as, without limitation, water in liquid rate (WLR) and gas phase fraction, may include any or all of electromagnetic wave transmission, reflection or resonance with amplitude, frequency or phase or their derived quantities as measurands.

Figure 2:
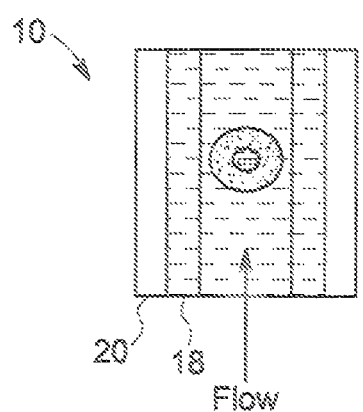
FIG. 2 is a side view of the material constituent sensor depicted in FIG. 1.

Metamaterials as described herein, are artificially structured materials that obtain their properties from their unit cell structure rather than from the constituent materials and in effect have a negative refractive index. These are artificial materials structured on a sub-wavelength scale to provide electromagnetic properties beyond those available in nature. Metamaterial structures are prepared by combining a structure which has a strong electric field response like a wire structure for obtaining negative permittivity and a structure which has strong magnetic field response like SRR for obtaining negative permeability. Typical properties of a metamaterial include a negative magnetic permeability, a negative dielectric constant, or a negative refractive index (when the magnetic permeability and the dielectric constant are both negative) depending on the unit cell structure used for making the metamaterial FIG. 2 is a cross-sectional side view of the material property sensor 10 depicted in FIG. 1. According to one aspect, the metamaterial assisted sensors 12 and 14 depicted in FIG. 1, are combined with a protective line 18 and placed to probe a multiphase composition; and the sensor 10 is excited with radio frequency or microwave signals causing an EM field or evanescent waves to be generated by the excited material property sensor 10. The metamaterial helps to improve the transmission between the metamaterial assisted antennas 12 and 14. The material property sensor 10 is employed to measure material properties or material fractions associated with a mixture of two or more materials, for example, gas and liquid (oil/water) or an emulsion of oil and water flowing through a conduit/pipe 20.

More specifically, one or more of metamaterial assisted antennas 12, 14 are excited over a range of frequencies and the reflected and/or transmitted power is measured over that frequency range. The transmitted and reflected amplitude and phase of the signals depends on the permittivity of the medium inside the pipe 20 and is used to estimate the phase fraction of the mixture. Further, the quality factor (Q) of resonance and the amplitude of the resonance peak can also be used.

Each metamaterial assisted antenna may comprise an RF/microwave antenna with a feed structure, antenna structure, radome and antenna protection liner, according to one embodiment. Metamaterials or negative refractive index materials can be used in any or all of the radome, antenna backside and antenna protection liner portions of the sensor 10. Further, a fractal geometry based antenna structure can be implemented as described in further detail herein in which the fractal geometry is part of the antenna.

Metamaterial assisted antennas radiate at much lower frequencies compared to an equivalent sized conventional antenna, as the metamaterial enhances the antenna characteristics even though the antenna structure is electrically small. Hence compared to regular antennas where the size of the antenna is comparable to the wavelength, metamaterial antennas have a radiating structure much lesser than the wavelength and hence smaller size at a particular operating frequency.

According to one aspect, realization of EM or evanescent wave coupling is enhanced by arranging one or more pieces of metamaterial along the path of the EM or evanescent wave coupling between the transmitting antenna and the receiving antenna. The sensor 10 may comprise a structure such as a current loop that is configured to generate electromagnetic fields or evanescent waves which are non-radiative in nature. Metamaterial is arranged within the resultant electromagnetic (EM) near-field such that the coupling between the transmitting antenna/transmitter and receiving antenna/receiver is enhanced. This more efficient energy coupling increases transmission amplitude of the EM fields or evanescent waves, enhancing fields in the flowing medium of interest.

Figure 3:
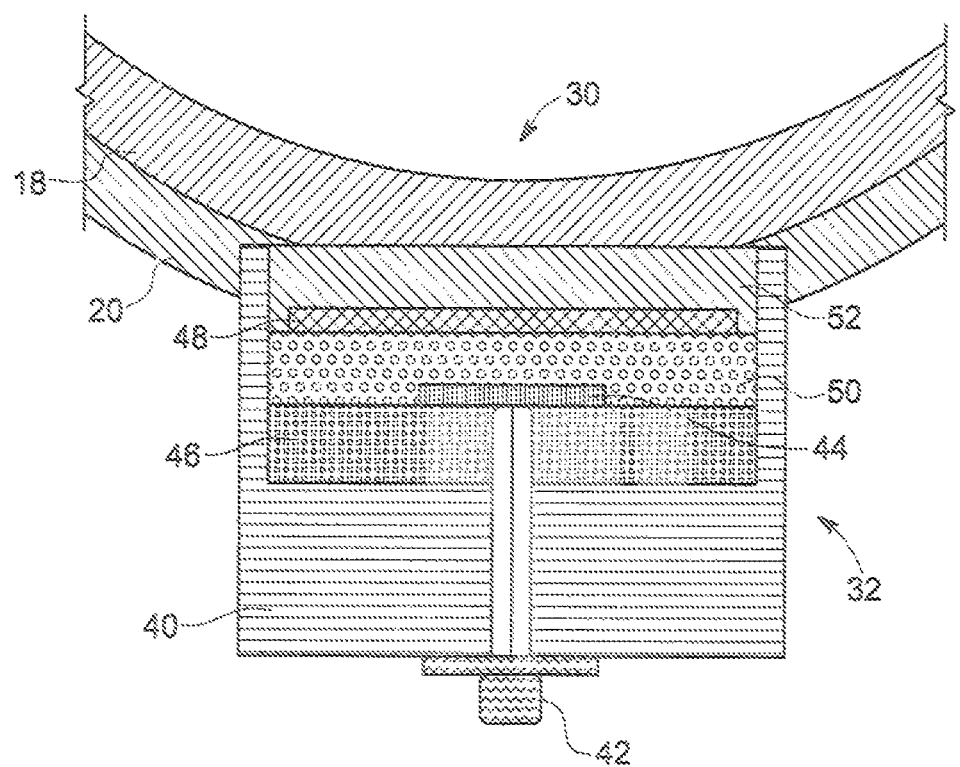
FIG. 3 is a more detailed view of a metamaterial assisted antenna suitable for use with the sensor depicted in FIG. 1.

FIG. 3 is a more detailed view of a metamaterial assisted antenna structure 30 according to one embodiment, and comprises at least one metamaterial assisted antenna 32. A sensor transmitting antenna, receiving antenna or both may be metamaterial assisted antennas. Further, metamaterials may be employed in any or all of the antenna 32, radome 52 and liner portions 18 of the metamaterial assisted antenna structure 30, as stated herein. A single structure common to both transmitting and receiving antennas will be assumed for purposes of describing one embodiment of a metamaterial assisted antenna herein. Those skilled in the art will appreciate that other embodiments can employ a receiving antenna structure that is different than the transmitting antenna structure to achieve the principles described herein.

Metamaterial assisted antenna structure 30 comprises an antenna liner 18 disposed within a conduit/pipe 20. According to one embodiment, a metal antenna holder 40 encases and supports the various components of the antenna 32. According to one embodiment, an RF connector 42 is attached to the metal holder 40 and is electrically connected to a feed element 44. The feed element can be used to directly excite or electromagnetically excite the antenna structure. It can be appreciated that feed element 44 may instead be an antenna radiating element or receiving element in alternative embodiment. Antenna 32 further comprises a radiating element 48 that may be configured as a transmitting element or a receiving element, depending upon the particular application.

According to one embodiment, a radome 52 is positioned within holder 40 to provide environmental protection for the radiating element 48. Any one or more of radiating element 48, radome 52 or liner 18 may comprise metamaterials depending upon the particular application.

According to one embodiment, the antenna radiating element 48 comprises a fractal geometry. As used herein fractals are self-similar designs to maximize the electrical length or increase the perimeter of the structure within a given total surface area or volume. Fractal antennas due to their multilevel space filling curves are very compact, multiband or wideband depending upon the design. A fractal antenna has an excellent response at many different frequencies simultaneously which helps for multiband or wide band operation.

The embodiments described herein provide distinct technical advantages over known material property sensors. Some of these advantages include without limitation, enhanced miniaturization of the antenna structure, lowering of the operating frequency, evanescent wave coupling, beam focusing capability, and a wider frequency band due to use of fractal geometry.

Figure 4:
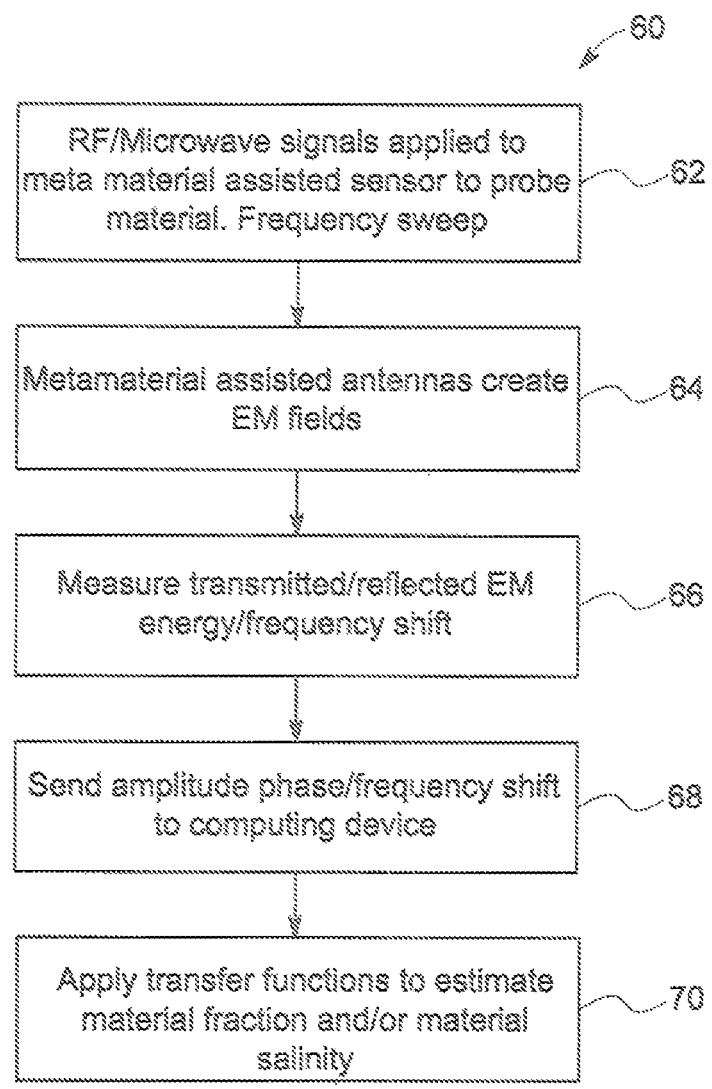
FIG. 4 is a flow chart depicting a method of measuring material constituents according to one embodiment.

FIG. 4 is a flow chart 60 depicting a method of measuring flow constituents according to one embodiment. The method 60 commences by first applying RF/microwave signals to one or more metamaterial assisted antennas that are positioned to probe a material as represented in step/block 62. A frequency sweep is performed within the desired RF/microwave band of frequencies as also depicted in step/block 62.

The transmitted and/or reflected electromagnetic energy and/or frequency shift is then measured in response to the EM field(s) generated by the one or more metamaterial assisted antennas during the frequency sweep as represented in steps/blocks 64 and 66.

The resultant amplitude/phase/frequency shift signals that are measured in step/block 66 are then transmitted to a flow computer as represented in step/block 68. The flow computer is programmed with transfer functions that are applied by the flow computer to estimate without limitation, constituent fractions of a material such as a multiphase mixture that may be fixed or flowing in a pipeline or conduit, as represented in step/block 70. The constituents may comprise without limitation, water fraction and gas fraction of the multiphase mixture that is flowing in the pipeline or conduit of interest. Salinity may also be estimated from the measured signal data for a material, for example, that is not a multiphase mixture.

In summary explanation, metamaterials are used in the construction of a material constituent sensor 10 that operates in the RF/microwave region of the electromagnetic spectrum. The sensor 10 measures reflected and/or transmitted power characteristics and/or frequency shift of signals passing through a single material or mixture of two or more materials, for example, gas and liquid (oil/water) or an emulsion of oil and water that may be fixed or flowing in a pipe/conduit. Fractal geometry can be employed in the sensor as described herein to further enhance its performance by facilitating sensor operation over a wider band of frequencies.

Figure 5:
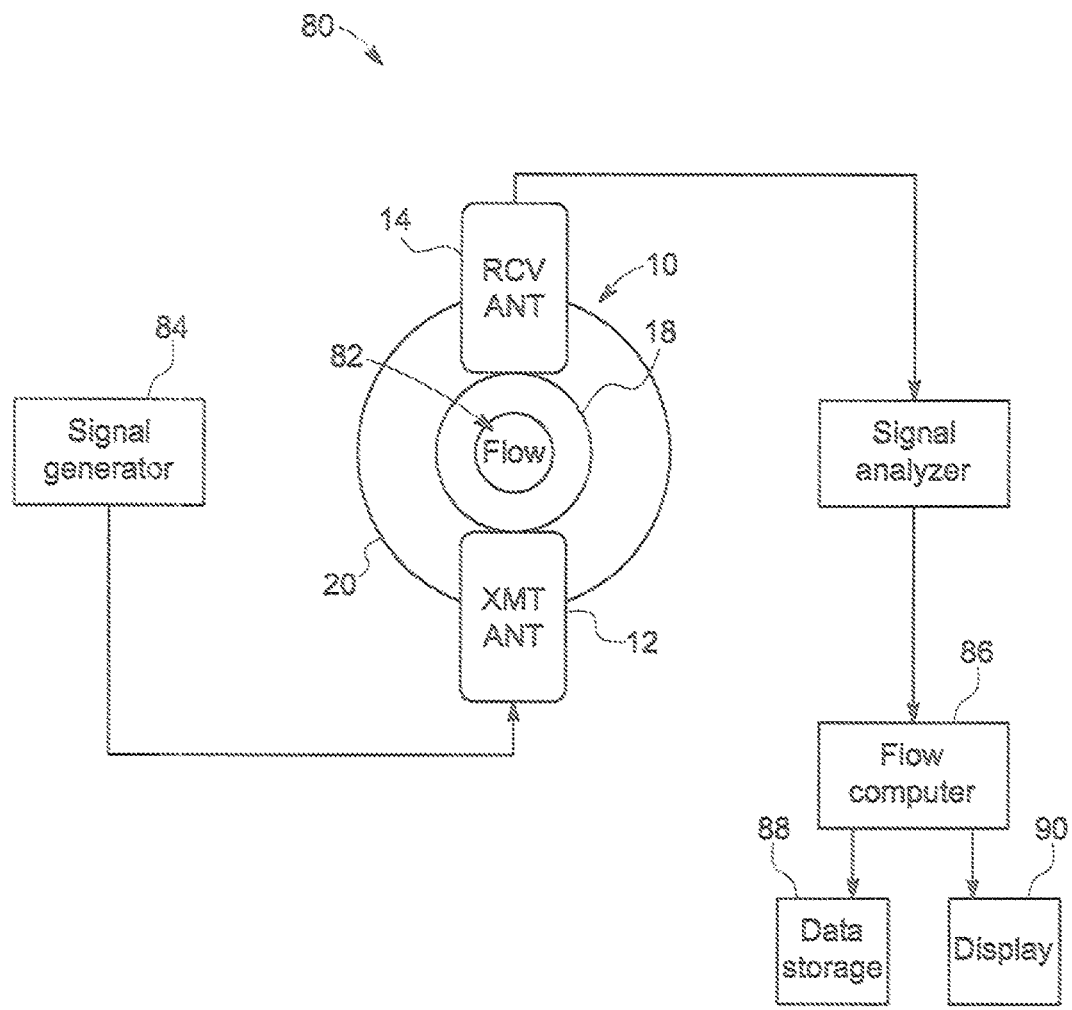
FIG. 5 is a diagram illustrating a material constituent sensing system according to one embodiment.

FIG. 5 is a diagram illustrating a material flow constituent measurement system 80 according to one embodiment. Material flow constituent measurement system 80 comprises a material flow constituent sensor 10 that comprises a transmitting antenna 12 that may comprise metamaterial(s), a receiving antenna 14 that may comprise metamaterial(s), and an antenna protection liner 18 that may comprise metamaterial(s). At least one of the transmitting antenna 12, receiving antenna 14, and protection liner 18 comprises metamaterial. The sensor 10 is positioned relative to a conduit/pipe 20 to measure constituent fractions of one or more multiphase compositions 82 fixed or flowing in the conduit/pipe 20. Sensor 10 may also be employed to measure material salinity, as stated herein.

One method of measurement commences by first applying RF/microwave signals to the transmitting antenna 12 that is placed to probe a material 82. The RF/microwave signals are generated by a signal generator 84. Using the signal generator 84, a frequency sweep is performed within the desired RF/microwave band of frequencies based upon the application.

Transmitted and/or reflected electromagnetic energy and/or frequency shift is then measured in response to the EM field(s) generated by the transmitting antenna 12 during the frequency sweep. More specifically, the receiving antenna 14 is coupled to the transmitting antenna 12 via EM fields that are influenced by the material fractions inside the pipe. The resultant amplitude and phase signals sensed by the receiving antenna 14 are transmitted to a computer or data processing device 86 that is programmed with transfer functions that are applied by the computer or data processing device 86 to estimate without limitation, material fractions of the fixed or flowing material 82 such as a multiphase mixture flowing in a pipeline or conduit 20. The material fractions may comprise without limitation, liquid fraction and gas fraction. Other material properties such as, without limitation, material salinity can also be determined for a material that is not a multiphase material. The estimated material properties or material fractions are then stored in a data storage device/system 88 and/or transmitted to a display device/unit 90 for use by an operator.

Figure 6:
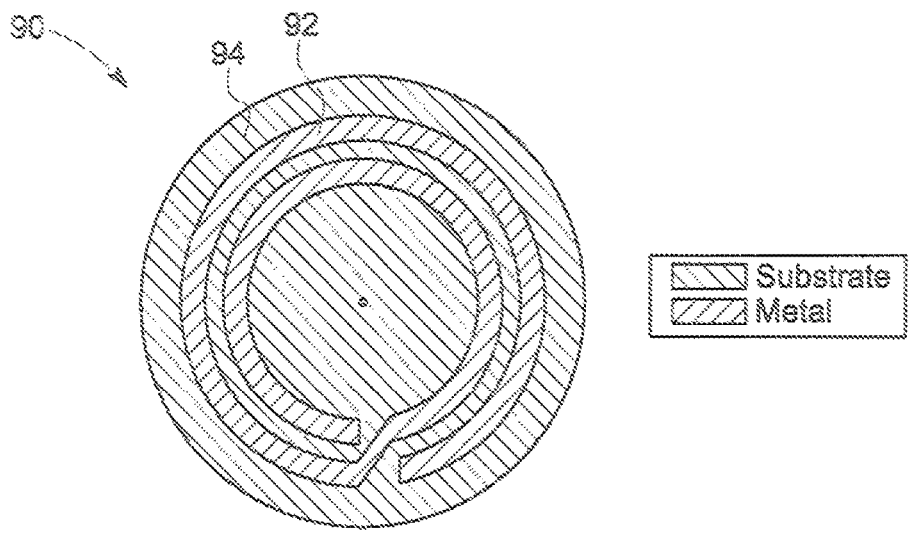
FIG. 6 is a diagram illustrating a representative spiral element type antenna suitable for use in a metamaterial assisted antenna application to form a material constituent sensor according to one embodiment.

FIG. 6 is a diagram illustrating a representative spiral element type antenna 90 suitable for use in a metamaterial assisted antenna application to form a material constituent sensor according to one embodiment and using the principles described herein. Spiral element type antenna 90 comprises a metal spiral 92 integrated with a suitable substrate 94. The particular metal 92 and substrate 94 material used to construct the antenna 90 are based upon the application.

Figure 7:
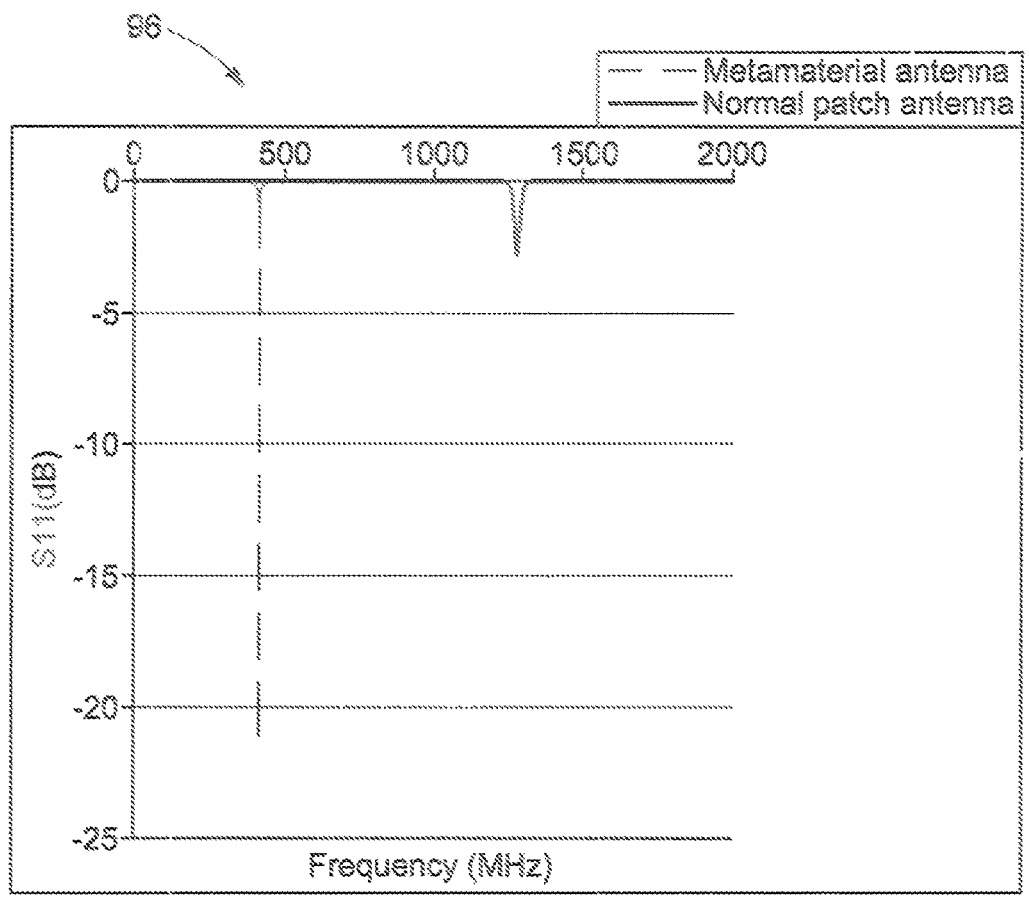
FIG. 7 is a graph illustrating reflection coefficient as a function of frequency for a normal patch antenna when compared to a spiral element type antenna according to one embodiment.

FIG. 7 is a graph 96 illustrating reflection coefficient as a function of frequency for a conventional patch antenna when compared to a spiral element type antenna such as antenna 90 depicted in FIG. 6, according to one embodiment. The conventional patch antenna of similar dimensions radiates at 1700 MHz, while the spiral element antenna 90 radiates at 400 MHz. A spiral element antenna thus can be much smaller than a conventional patch antenna of similar radiation frequency.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A method of material constituent measurement, the method comprising:
   providing at least one metamaterial assisted sensor, each sensor comprising at least one antenna configured as a transmitter of electromagnetic (EM) energy, a receiver of EM energy, or a combination thereof, wherein a metamaterial of the at least one metamaterial assisted sensor comprises a negative refractive index;
   placing at least one metamaterial assisted sensor inside a conduit to probe a material;
   exciting at least one metamaterial assisted sensor via a signal source at one or more frequencies;
   measuring a transmitted energy level, a reflected energy level, a frequency shift, or a combination thereof in response to the sensor excitation; and
   applying transfer functions to estimate via a programmable computing device, one or more material fractions associated with the probed material based on amplitude data, phase data, frequency shift data or a combination thereof in response to the transmitted energy level, reflected energy level, a measured frequency shift, or combination thereof to determine a gas fraction and a liquid fraction.

2. The method according to claim 1, further comprising estimating via the programmable device, probed material salinity.

3. The method according to claim 1, wherein the one or more material fractions comprise a water fraction.

4. The method according to claim 1, wherein the probed material is flowing within a conduit.

5. The method according to claim 4, wherein placing at least one metamaterial assisted sensor to probe a material, comprises placing a liner configured with metamaterial inside a desired portion of the conduit through which the probed material is flowing.

6. The method according to claim 1, wherein the probed material comprises a multi-constituent material.

7. The method according to claim 6, further comprising applying transfer functions via the programmable computing device to estimate constituent fractions of the probed multi-constituent material.

8. The method according to claim 1, wherein providing at least one metamaterial assisted sensor further comprises placing a liner configured with metamaterial inside a desired portion of a conduit through which the probed material can flow, placing a radome configured with metamaterial around at least a portion of one or more antennas, or a combination thereof.

9. The method according to claim 1, wherein measuring a transmitted energy level, a reflected energy level, a frequency shift, or a combination thereof in response to the sensor excitation comprises measuring signal characteristics in a radio frequency range, a microwave range, or a combination thereof.

10. The method according to claim 1, wherein providing at least one metamaterial assisted sensor comprises providing at least one metamaterial assisted antenna and at least one non-metamaterial assisted antenna when the metamaterial assisted sensor comprises a plurality of antennas.

11. A material constituent sensor, comprising:
one or more metamaterial assisted sensors placed inside a conduit to probe a material, wherein each metamaterial assisted sensor comprises at least one antenna configured as a transmitter of electromagnetic (EM) energy, a receiver of EM energy, or a combination thereof, and wherein a metamaterial of the at least one metamaterial assisted sensor comprises a negative refractive index;
a signal source configured to excite at least one metamaterial assisted sensor in a desired range of radio frequency signals, a desired range of microwave signals, or a combination thereof; and
a programmable computing device configured to estimate one or more material fractions associated with the probed material based on amplitude data, phase data, frequency shift data, or a combination thereof in response to transmitted energy from at least one sensor antenna, reflected energy received by at least one sensor antenna, or a combination thereof to determine a gas fraction and a liquid fraction.

12. The material constituent sensor according to claim 11, wherein at least one antenna is configured with metamaterial.

13. The material constituent sensor according to claim 12, wherein at least one antenna is a non-metamaterial antenna when the material property sensor comprises a plurality of antennas.

14. The material constituent sensor according to claim 11, wherein at least one antenna comprises at least a portion thereof sealed by a radome configured with metamaterial.

15. The material constituent sensor according to claim 11, wherein at least one antenna comprises a fractal geometry.

16. The material constituent sensor according to claim 11, wherein the programmable computing device is further configured to estimate probed material salinity.

17. A material constituent sensor comprising:
one or more metamaterial assisted sensors placed inside a conduit to probe a material, wherein each metamaterial assisted sensor comprises:
at least one antenna configured as a transmitter of electromagnetic (EM) energy, a receiver of EM energy, or a combination thereof,
wherein a metamaterial of the at least one metamaterial assisted sensor comprises a negative refractive index, and
wherein the sensor is configured to determine a gas fraction and a liquid fraction.

18. The material constituent sensor according to claim 17, wherein at least one antenna is configured with a fractal geometry.

19. The material constituent sensor according to claim 17, further comprising a liner configured with metamaterial disposed inside a desired portion of a conduit through which the material to be probed is flowing.

20. The material constituent sensor according to claim 17, further comprising a programmable computing device configured to estimate one or more constituent fractions associated with the probed material based on amplitude data, phase data, frequency shift data, or a combination thereof in response to transmitted energy from at least one sensor antenna, reflected energy received by at least one sensor antenna, or a combination thereof.

* * * * *